United States Patent
Kumakhov et al.

(10) Patent No.: US 7,118,671 B2
(45) Date of Patent: Oct. 10, 2006

(54) POLYCAPILLARY CHROMATOGRAPHIC COLUMN AND METHOD OF ITS MANUFACTURING

(75) Inventors: Muradin A. Kumakhov, Moscow (RU); Valery B. Zheltov, Moscow (RU); Boris A. Rudenko, Moscow (RU); Ruslan Kh. Khamizov, Moscow (RU); Nikolay P. Shoromov, Moscow (RU); Oleg O. Nayda, Moscow (RU)

(73) Assignee: Institute for Roentgen Optics, Moscow (RU)

( * ) Notice: Subject to any disclaimer, the term of this patent is extended or adjusted under 35 U.S.C. 154(b) by 83 days.

(21) Appl. No.: 10/788,291

(22) Filed: Mar. 1, 2004

(65) Prior Publication Data

US 2004/0217043 A1   Nov. 4, 2004

(30) Foreign Application Priority Data

Apr. 30, 2003   (RU)   ............................... 2003112601

(51) Int. Cl.
*B01D 15/08*   (2006.01)
(52) U.S. Cl. .................................... 210/198.2; 210/656
(58) Field of Classification Search ............. 210/198.2, 210/656, 659; 96/101, 105
See application file for complete search history.

(56) References Cited

U.S. PATENT DOCUMENTS 6,766,817 B1   7/2004   daSilva

FOREIGN PATENT DOCUMENTS

| SU | 1635128 | 3/1991 |
|---|---|---|
| SU | 1635129 | 3/1991 |
| SU | 1651200 | 5/1991 |
| SU | 986181 | 8/1991 |

OTHER PUBLICATIONS

PTO 2005-5468, Translation of SU 1635129, Aug. 2005.*
PTO 2005-5620, Translation of SU 986181, Aug. 2005.*

(Continued)

*Primary Examiner*—Ernest G. Therkorn
(74) *Attorney, Agent, or Firm*—McDermott Will & Emery LLP

(57) ABSTRACT

Polycapillary chromatographic column contains a set of parallel channels isolated from each other, walls of the channels on the inside are covered with sorbent, and are joined with walls of adjacent channels on the outside by fusing. Feature of a column is that it is produced as set of modules of a various level, thus the module of the lowest level represents hexagonally packed and having in cross-section shape of a correct hexagon set of the channels which are produced by joint drawing of a bundle of monocapillaries in the softened condition. The module of each higher level represents hexagonally packed and having in cross-section shape of a correct hexagon set of modules of the previous level, growing out by their joint drawing in the softened condition. All modules of the highest level (the modules are made in shells 2 on the drawing) are grouped in the uniform hexagonally packed structure (on the drawing it is surrounded with an external protective shell 3), produced by their joint drawing in the softened condition.

The method of columns manufacturing consists in realization of several stages drawing of blanks packages, each of which is drawing result at the previous stage, and cuttings produced at drawing items on a part of the specified length—blanks.

The micrometer and submicrometer size of channels are achieved at their number equal 1 million in order of magnitude with small dispersion of the channel diameters.

11 Claims, 3 Drawing Sheets

OTHER PUBLICATIONS

PTO 2005-5619, Translation of SU 1651200, Aug. 2005.*
PTO 05-5605, Translation of Tesacik, Aug. 2005.*
PTO 05-5606, Translation of Rudenko, Aug. 2005.*
PTO 2005-5616, Translation of SU 1635129, Aug. 2005.*

Tesarzhik K. et al., "Capillary columns in gas chromatography" (in Russian, translation from Czech), 1987, pp. 5, 6, Publishing house "MIR," Moscow.

Rudenko B.A., "Capillary chromatography" (in Russian), 1978. pp. 14, 15, Publishing house "Nauka," Moscow.

* cited by examiner

POLYCAPILLARY CHROMATOGRAPHIC COLUMN AND METHOD OF ITS MANUFACTURING

BACKGROUND OF THE INVENTION

1. Field of the Invention

Proposed inventions are related to area of analytical chemistry, namely to a chromatography and to fabrication methods of the chromatography equipment elements, more concrete—to the chromatographic column and method of its manufacturing.

2. Description of Related Art

One of modern tendencies of analytical chemistry is a miniaturization of chromatographic equipments, including use of capillary columns in the chromatography (Tesarszik K., Komarek K. Capillary columns in gas chromatography (in Russian—translation from Czech).—Moscow, Publishing house "Mir", 1987, 222 p. [1]). Using the capillary columns with a sorbent located on internal walls has allowed to increase specific and general efficiency of achievable separation, to reduce sorbent consumption, to increase considerably sensitivity of chromatographic analytical system and to improve such characteristics of process as a radial gradient of temperature at programming, to simplify realization of hyphenated method of the gas chromatography analysis in a combination with mass-spectrometry.

Separation of substance sample on its components in a chromatography is determined by two characteristics of chromatographic column—its selectivity and efficiency. Measure of selectivity is relative retention of separated components, and measure of efficiency is characterized by number of so-called theoretical plates. Basic advantage of the chromatographic capillary columns is that on absolute and relative efficiency of these columns essentially surpass traditionally used chromatographic packed columns having diameter more then 2 mm. Total efficiency of capillary columns is 30000–100000 theoretical plates, and more (Rudenko B. A. Capillary chromatography (in Russian)—Moscow, Publishing house "Nauka", 1978.—215 p. [2]) that much more surpasses efficiency of the packed columns.

Together with such advantage as high efficiency of sample components separation, chromatographic capillary columns have the disadvantage consisting in significant restriction of the sample's weight. It reduces a signal magnitude at the analysis and sharply increases the limit of determined concentration.

This advantage is reduced in polycapillary (multichannel) chromatographic columns, being a package of 1000–2000 capillaries of diameter from 30 up to 100 micrometers located in parallel to each other (the inventor's certificate of the USSR No968181, issued 15.08.91 [3]; inventor's certificate of the USSR No1635128, issued 15.03.91 [4]; patent of the Russian Federation No1651200, issued 23.05.91 [5]).

However, when the column has such limited number of capillaries, then even insignificant distinctions in amount of the deposited mobile phase in them result in occurrence of a significant dispersion of retention times of substances. The dispersion essentially reduces efficiency of separation achievable with the aid of such columns. As a result, the efficiency of such columns stops increase when their length surpasses 1.0–1.5 m.

In inventor's certificate of the USSR No1635128 (issued 15.03.91 [6]) the method of manufacturing polycapillary chromatographic columns is proposed. The method's purpose is increasing uniformity of the columns' flow areas. The method provides manufacturing a column by softening and drawing bank of blanks formed from cylindrical rods of identical size. The rods forming central part of the blank of each separate channel are made from a technological material, should be later removed. Rods, surrounding the central part, are produced from the base material. These rods after removing the technological material form a walls of the channel. A package of blanks is formed in a way, providing hexagonal or square packing the rods' group Known method on the inventor's certificate of the USSR No1635129 (issued 15.03.91 [7]) in comparison with previous is more complicated. Some of the rods surrounding rods of the blank's central part of the single channel are also produced from the technological material. After removing the technological material, it results in formation of longitudinal grooves in walls of the channels. The grooves connect the joint channels with each other.

Thus, polycapillary chromatographic columns made by the methods, known from [6] and [7], contain set of the parallel channels. The channels are joined by fusion of external walls of the adjacent channels. At that in the column made by the method known from [6], channels are isolated from each other, and in a column known from [7] the adjacent channels are connected with each other by means of longitudinal grooves in their walls.

Polycapillary chromatographic columns made according to the specified methods require large labor-consumption. The large labor-consumption is caused by the necessity of manual forming the blank of each channel. At that, it is not possible to produce the blank having channels number exceeding provided in known columns [3–5]. Therefore, further increase of the chromatographic column parameters is impossible. Therefore, realization of advantage of the manufacturing methods known from [6, 7] is impossible too.

Polycapillary chromatographic column and method of its manufacturing known from the inventor's certificate of the USSR No1635128 [6] are closest to the proposed column and method.

SUMMARY OF THE INVENTION

The technical result, which would be provided by proposed inventions, consists in producing chromatographic columns with the channels' of submicron cross-section sizes. At that the channels number is increased up to hundreds of thousands and more with corresponding substantial increase of efficiency due to increase in a total surface of walls of channels. The manufacturing techniques of polycapillary chromatographic columns on offered method simultaneously provides reduction of dispersion of the channel cross-section size.

Proposed polycapillary chromatographic column, as well as the closest to it column [6], contains set of parallel channels isolated from each other. The channel walls internal surface is covered with a sorbent. The walls external surfaces are joined by fusing with adjacent channels.

To achieve specified technical result the proposed polycapillary chromatographic column, as against the known column closest to it, is produced as set of modules of a various level. At that, the module of lowest level represents hexagonally packed and having in cross-section correct hexagonal shape set of the channels. This set is result of mutual drawing the bank of monocapillaries in softened condition At that the module of each higher level represents hexagonally packed and having in cross-section the correct hexagonal shape set of the modules of previous level. This set is result of mutual drawing the modules in the softened condition. All modules of the highest level are arranged in the uniform hexagonally packed structure, which is the result of their joint drawing in softened condition.

To increase mechanical strength of the column the modules of each levels can have a shell, produced from the same material, as a wall of channels, or from material close to it on thermal expansion factor.

All modules of the highest level can be arranged in the common shell. The shell is external protective one of polycapillary chromatographic column.

The walls of channels, external protective shell and shells of modules of all levels can be produced from a glass, ceramics, or metal.

The offered method of column manufacturing, as well as the known method closest to it from the inventor's certificate [6], includes drawing the hexagonally stacked package of the blanks, which have been heated up in the furnace to the material softening temperature.

To achieve the mentioned above technical result the proposed method, as against the closest to it known one, is performed in several stages, on the each stage a package of earlier made blanks is formed. At the first stage monocapillaries are used as blanks. At each of the subsequent stages—the blanks received as a result of realization of the previous stage are used. In the process of drawing prepared package the rate of its feeding to a furnace is lower, than withdrawal rate of the article from the furnace, at a constant ratio between these rates. Blanks, which are leaving furnace at the given stage, are cut on specified length. And after sorbent deposition to the channels internal surface, the process of polycapillary chromatographic column production is finished.

In the proposed method during formation of the blank package the blanks are arranged in parallel lines so that the difference of quantity of blanks in any two next lines was odd. For all stages, except the last one, at stacking the package a mandrel is used. The mandrel has shape of correct hexagonal prism. At last stage the prism's shape not necessary should be hexagonal and correct. The stacking of blanks could be performed into tubular container of the desirable shape. At the last case for formation of a flat side on which the first line of blanks is stacked, the loose leaf is inserted into the specified container. The loose leaf on the one side is congruous with the container, and on the other one is flat.

To increase mechanical strength of the polycapillary columns the blanks, produced at each stage and subjected to stacking in a package at the following stage, are made with shells. For this purpose at the package stacking the solid rods are put on its periphery at formation of the blanks package. The rods are identical with blanks on the shape. They have geometrical sizes and the linear expansion coefficient of their material identical or close to the blanks' sizes and their material linear expansion.

Performance of such operation at the package formation that is subjected to drawing at last stage of the method realization results in production of polycapillary chromatographic columns, encased into external protective shell. If the package subjected to drawing at last stage of the method is formed by stacking blanks into the tubular container, then the external protective shell is produced in result of the drawing tubular container together with a package of blanks inserted in it.

A glass, ceramics or metal can be applied as a material of the monocapillaries, used as blanks at the first stage for production the shells of different level modules and external protective shells, and also complete polycapillary chromatographic columns.

BRIEF DESCRIPTION OF THE DRAWINGS

Proposed inventions are illustrated by drawings on which there are presented:

On FIG. 1—a schematic cross-section view of polycapillary chromatographic column;

Figure 2:
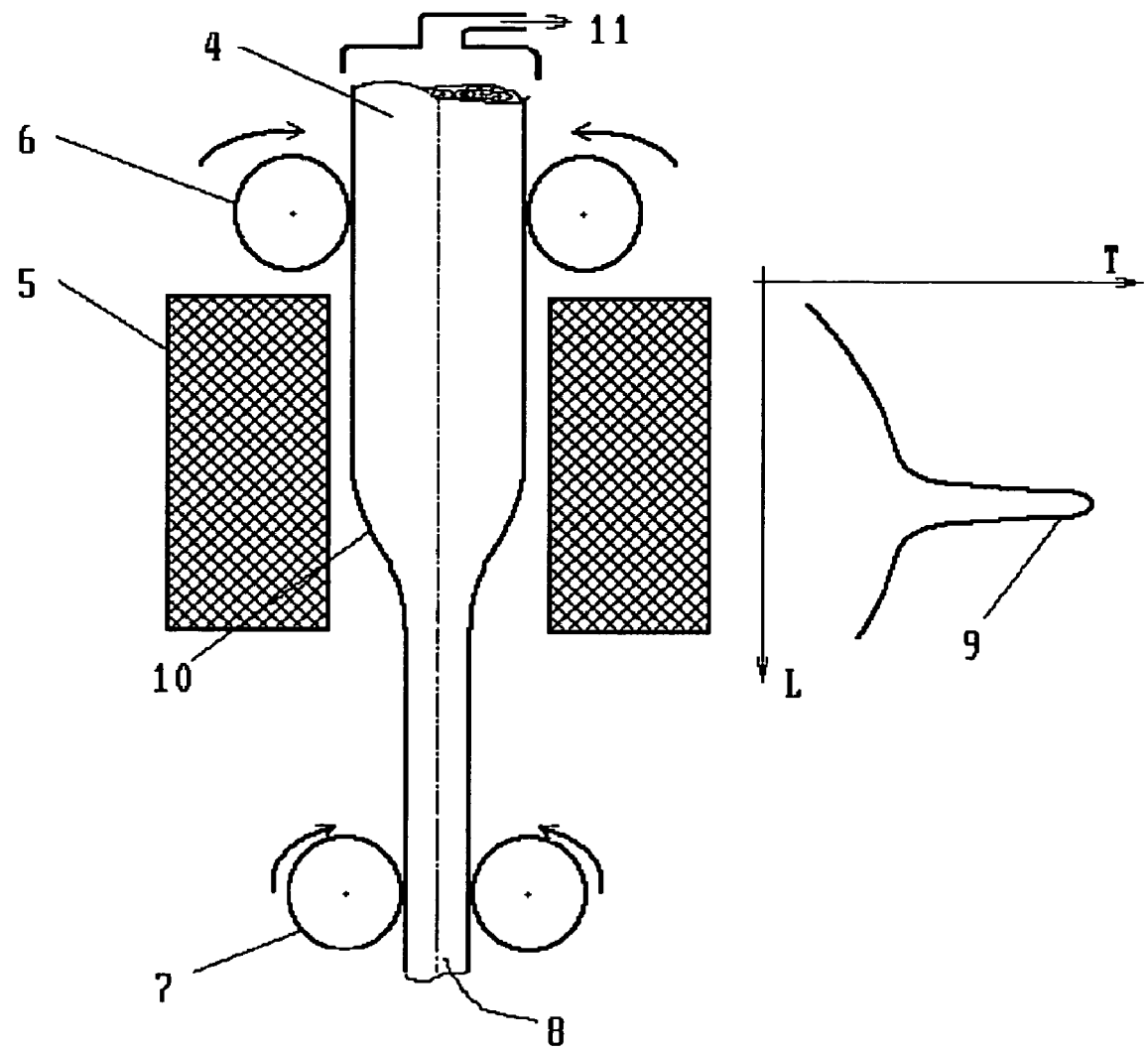
Figure 3:
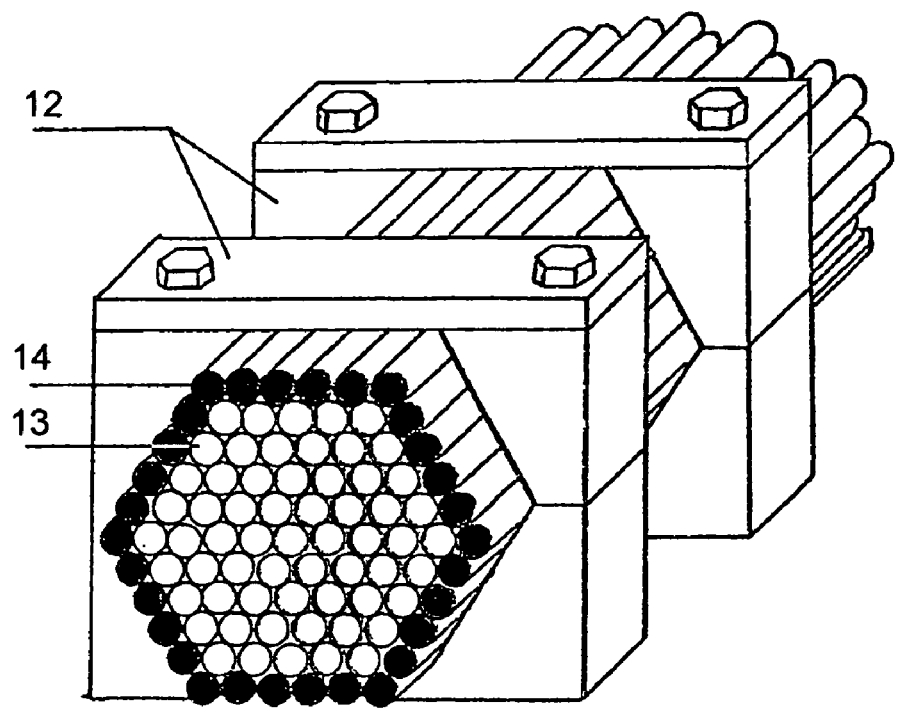
Figure 4:
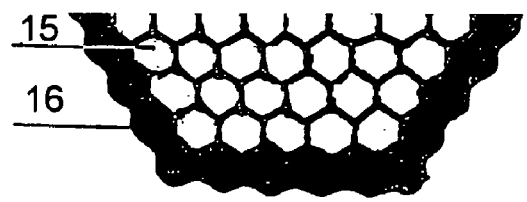
Figure 5:
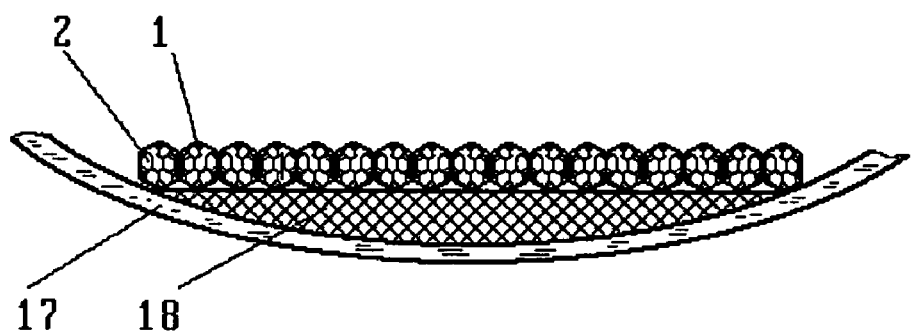

On FIG. 2—process of drawing;

On FIG. 3—process of the formation of blank package for first stage of the method;

On FIG. 4—the form of blank cross-section received as a result of the first stage of method;

On FIG. 5—use of the loose leaf at stacking the blanks' package at the final stage of method in a tubular container.

DETAILED DESCRIPTION OF THE PREFERRED EMBODIMENTS

Figure 1:
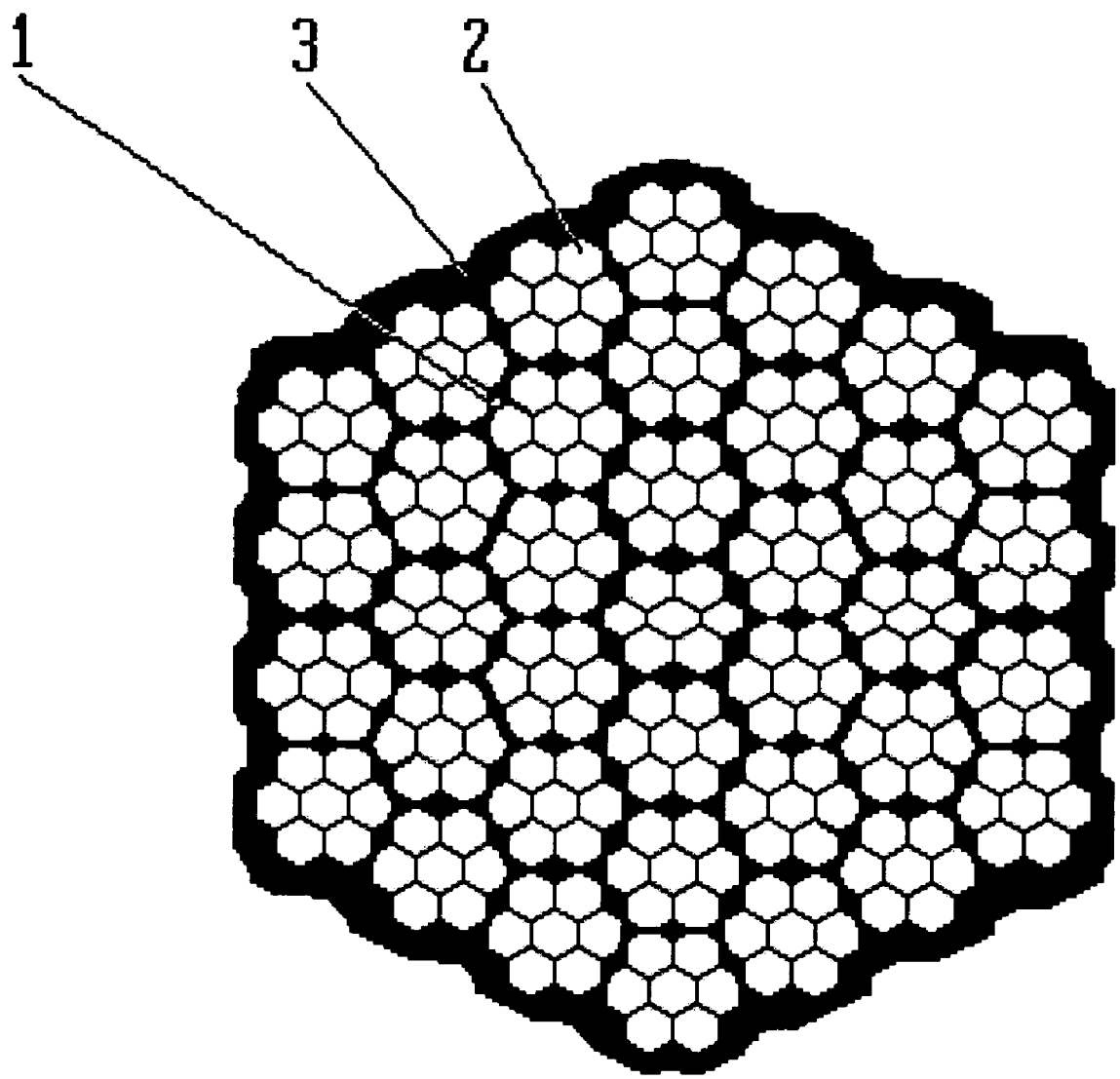

On FIG. 1, modules of a highest level with shells 1 are presented. Each of these modules is formed by group of modules 2 of the previous level. On FIG. 1, each module of a highest level is conditionally shown consisting of seven modules of the previous level (actually their number is much more; the scale of the drawing does not allow to show also their internal structure with modules of lower levels). All modules of a highest level grouped in uniform hexagonal structure and placed in the common protective shell 3, forms chromatographic column.

It is necessary to pay attention on the design of proposed polycapillary chromatographic column, which does not represent simple result of assembly in direct sequence. At the first stage the channels-monocapillars are joined into modules of the first level, then the modules are grouped as modules of the second level, etc. The structure is inextricably related with the offered method of manufacturing polycapillary chromatographic columns. Modules of the levels and polycapillary chromatographic column are produced only as the result of the method realization as a whole, after several stages of drawing. It is impossible to disassembly the produced polycapillary chromatographic column on modules of different level and on separate channels.

To produce described polycapillary chromatographic columns by the proposed method, a package of blanks 4 (FIG. 2), for example, glass one, prepared at the previous stage of the method is fed vertically into furnace 5 with the help of the top drive 6. Then the package is drawing from the furnace at rate exceeding speed of feed, with the help of bottom drive 7. Resulted item 8 has essentially smaller cross-section size, than the package 4 on the furnace input. Temperature in the furnace should be sufficient for a softening the material and fusing adjacent blanks, forming package 4. At the first stage monocapillaries, in particular, glass ones, are used as blanks, which form the package. Glass monocapillaries as itself could be produced with similar method by drawing the glass tubes with their subsequent cutting on pieces of the specified length.

At drawing in the furnace, axial symmetric temperature field is provided. The temperature field has shown on FIG. 2 distribution of temperature T on height L of the furnace, and a narrow maximum 9. The area of transition 10 of the blanks package 4 having initial cross-section size to smaller diameter of the article 8 is in the zone of narrow peak 9 of temperature distribution along furnace height.

To prevent capillaries flattening ("closing") during the drawing process, accompanying with compression of blanks, the pressure in space between the blanks is maintained at a value, lower, than the pressure inside blanks channels. It is important to maintain the value of pressure in channels of module capillaries of the lowermost level higher, than the pressure in the specified space. For this purpose, it is necessary to close the top ends of channels of blanks before the package formation (for example, by fusing the top ends of the blanks), and at the drawing process, is necessary vacuumization of the package (evacuating gases) through the top end face of the blanks' package (the pumping out is schematically shown by an item 11 on FIG. 2). Sealing of the bottom ends of blank channels is not necessary. The sealing is provided due to essential reduction of the cross-section size of the package leaving the furnace in comparison with the cross-section size of the blanks' package fed to the furnace from top.

Produced by drawing the article after cooling is cut. The obtained pieces are blanks for the following stage. They are again formed into a package and drawn, like in previous stage.

Process of formation of the package of blank-capillaries for carrying out the first stage of offered method is shown on FIG. 3 for a special case when modules of the first level should have a shell. On FIG. 3 there are shown demountable mandrel 12, having apertures as exact hexagonal prisms, and blanks (in this case—circle monocapillaries 13 and solid rods 14 of same diameters). The solid rods 14 (on the drawing are black) located on periphery of the package are intended for formation shell of the module (in this case—the module of the first level). Blanks are stacked in the horizontal layers parallel to the bottom horizontal sides of apertures of mandrel 12. The quantity of blanks in any two adjacent layers differs on odd number.

In result of drawing on the diagram shown on FIG. 2, round capillaries turn to channels 15 (FIG. 4), having a shape close to hexagonal. On the drawing the shell 16 of blanks is shown, the shell is produced at the first stage of the method. It is intended for use at formation of a package of the second stage. At the drawing process in the diagram of FIG. 2, sectional mandrels (on FIG. 2 are not shown) are removed from a package 4 during process of its feeding into a furnace 5.

At subsequent stages of the method the packages are formed in a way that is similar to one shown on FIG. 3, and a difference is that now the blanks having shape close to hexagonal are used. Formation of the package for the method's final stage can differ in aperture shape of used mandrels. The mandrel not necessarily should have the shape of correct hexagonal prism and its shape can represent a convex polygon in cross-section; one of the polygon sides at beginning of the package formation process should be located in horizontal plane. At this stage, the package can be formed also by hexagonal stacking of blanks into a tubular container 17 (FIG. 5) having specified cross-section shape. Absence of a flat side of the tubular container can be compensated by inserting into the container the loose leaf 18, that is on one side congruous with the container, and on the other side-flat. The first line of blanks (in this case—modules of a highest level with the shells 1, the modules formed by groups 2 of the previous levels) is stacked on a flat surface of the loose leaf 18.

Hexagonal stacking of round blanks at the first stage provides the greatest permeability of the first level modules. Use of hexagonal shape blanks and their hexagonal stacking at the subsequent stages provide the most dense packing channels. And all these actions, hence, provide the greatest permeability of produced columns as a whole, including the columns having polygonal form of cross-section. That shape differs from the correct hexagon, or at package stacking into a tubular container for last stage of the method too. Features of the described technology provide small dispersion of the cross-section size of channels-capillaries.

When the column is intended for use in a gas chromatography, then sorbent layer is deposited onto the walls of channels-capillaries by supplying 3–10%—sorbent solution in organic solvent through the column's channels and subsequent evaporation of the solvent by inert gas flow.

Column specified for use in a liquid chromatography, should have etched walls of channels-capillaries. Suitable agent, for example, 20% NaOH-solution or the concentrated ammonia at increased temperature, should be used for the etching. Then the etching agent is washed out with pure water.

In finished pre-production models of polycapillary columns, the channel cross-section size value is 1 micron at the channels number about 1 million.

So large number of channels of midget diameter provides essential increase in the sensitivity of chromatographic analysis due to sharp increasing walls' total surface of the column channels.

It is experimentally confirmed, that uniform laying a stationary phase on walls of channels is provided at solution supplying through them.

In experiments on a gas chromatography at length of columns 400 mm the efficiency of 2–4 thousand theoretical plates or 5–10 thousand theoretical plates for one meter of the column length is achieved. In the liquid chromatography value of efficiency is about 1500 theoretical plates at length of a column of 100 mm.

REFERENCES

1. Tesarzhik K., Komarek K. Capillary columns in gas chromatography (in Russian, translation from Czech). Moscow, Publishing house "MIR", 1987.—222 p.
2. Rudenko B. A. Capillary chromatography (in Russian).—Moscow, Publishing house "Nauka", 1978.—215 p.
3. USSR inventor's certificate No968181, issued. 15 Aug. 1991.
4. USSR inventor's certificate No1635128, issued. 15 Mar. 1991.
5. Patent of the Russian Federation No1651200, issued. 23 May 1991.
6. USSR inventor's certificate No1635128, issued. 15 Mar. 1991.
7. USSR inventor's certificate No1635129, issued. 15 Mar. 1991.

The invention claimed is:

1. A polycapillary chromatographic column comprising:
   a package of modules of n level, where n≧2;
   each of the modules of the n level including a package of modules of (n-1) level, each module of a first level including:
   a package of monocapillaries, each of the monocapillaries having a tubular wall; inner surfaces of walls of the monocapillaries being covered with a sorbent, outer surfaces of the walls being fused with each other; the monocapillaries providing isolated from each other parallel channels of the chromatographic column; and
   solid rods fused with each other for surrounding the package of the monocapillaries to provide a shell around the package of monocapillaries.
2. The column of claim 1, further comprising additional solid rods fused with each other for surrounding a package of modules of a level higher than the first level.

3. The column of claim 2, wherein the additional solid rods has the same cross-sectional size as each of the modules in the package surrounded by the additional solid rods.

4. The column of claim 2, wherein the additional solid rods are made of the same material as the monocapillaries.

5. The column of claim 2, wherein the additional solid rods have a linear expansion coefficient close or equal to a linear expansion coefficient of the monocapillaries.

6. The column of claim 1, further comprising an external protective shell surrounding the package of modules of n level.

7. The column of claim 1, wherein each of the modules of any level has a hexagonal cross-section.

8. The column of claim 1, wherein the package of the monocapillaries has a hexagonal cross-section.

9. The column of claim 1, wherein each of the solid rods has the same cross-sectional size as each of the monocapillaries.

10. The column of claim 1, wherein the solid rods are made of the same material as the monocapillaries.

11. The column of claim 1, wherein the solid rods have a linear expansion coefficient close or equal to a linear expansion coefficient of the monocapillaries.

* * * * *